US007309603B2

(12) United States Patent
Ma et al.

(10) Patent No.: US 7,309,603 B2
(45) Date of Patent: Dec. 18, 2007

(54) MULTIWELL PLATE LID WITH VENTS

(75) Inventors: Sha Ma, Cambridge, MA (US); Wang Hongming, Lee, NH (US)

(73) Assignee: Corning Incorporated, Corning, NY (US)

( * ) Notice: Subject to any disclaimer, the term of this patent is extended or adjusted under 35 U.S.C. 154(b) by 417 days.

(21) Appl. No.: 10/319,750

(22) Filed: Dec. 13, 2002

(65) Prior Publication Data

US 2004/0115798 A1 Jun. 17, 2004

(51) Int. Cl.
*C12M 1/18* (2006.01)
*B01L 3/00* (2006.01)

(52) U.S. Cl. .............................. 435/288.3; 435/305.3; 435/305.4; 422/102; 215/307

(58) Field of Classification Search ................ 422/101, 422/102; 435/286.6, 288.3, 288.4, 305.1, 435/305.2, 305.3, 305.4
See application file for complete search history.

(56) References Cited

U.S. PATENT DOCUMENTS

| | | | | |
|---|---|---|---|---|
| 5,780,294 | A | 7/1998 | Stevens et al. | 435/297.5 |
| 5,817,509 | A | 10/1998 | Stevens et al. | 435/297.5 |
| 5,863,972 | A | 1/1999 | Beckelmann et al. | 524/186 |
| 5,972,694 | A * | 10/1999 | Mathus | 435/288.4 |
| 2001/0024821 | A1 | 9/2001 | Potter | 435/297.5 |
| 2002/0054833 | A1 | 5/2002 | Qu et al. | 422/102 |

* cited by examiner

*Primary Examiner*—David Redding
(74) *Attorney, Agent, or Firm*—Thomas R. Beall; Susan S. Wilks; Larry A. Villaneuva

(57) ABSTRACT

Multiwell plates with lids that reduce evaporation in the wells adjacent the edge of the plates are disclosed. The lids control the amount of evaporation from the multiwell plate.

16 Claims, 3 Drawing Sheets

MULTIWELL PLATE LID WITH VENTS

FIELD OF THE INVENTION

This invention relates to the field of biological and chemical assays, and particularly to a multiwell device and lids used in such assays.

BACKGROUND OF THE INVENTION

The recent growth in many areas of biotechnology has increased the demand to perform a variety of studies, commonly referred to as assays, of biological and chemical systems. These assays include for example, biochemical reaction kinetics, DNA melting point determinations, DNA spectral shifts, DNA and protein concentration measurements, excitation/emission of fluorescent probes, enzyme activities, enzyme co-factor assays, homogeneous assays, drug metabolite assays, drug concentration assays, dispensing confirmation, volume confirmation, solvent concentration, and solvation concentration. Also, there are a number of assays which use intact living cells and which require visual examination.

Assays of biological and chemical systems are carried out on a large scale in both industry and academia, so it is desirable to have an apparatus that allows these assays to be performed in convenient and inexpensive fashion. Because they are relatively easy to handle, are low in cost, and generally disposable after a single use, multiwell plates, which are also called microplates, are often used for such studies. Multiwell plates typically are formed from a polymeric material and consist of an ordered array of individual wells. Each well includes sidewalls and a bottom so that an aliquot of sample may be placed within each well. The wells may be arranged in a matrix of mutually perpendicular rows and columns. Common sizes for multiwell plates include matrices having standardized dimensions of approximately 85 mm×128 mm with well capacities of 8×12 (96 wells), 16×24 (384 wells), and 32×48 (1536 wells).

Evaporation of the liquid contained in wells of multiwell plates with a conventional solid lid, especially multiwell plates with well capacities of 1536 wells or higher, within an incubator or on the countertop can exceed 15% to 25% in the corner wells and the wells on the outer periphery of the plate. The high amount evaporation from these wells of these plates causes dramatic changes in pH, nutrients, salt concentrations, etc. and cause what is called “the edge effect,” especially when cell based assays are performed.

Sealing tapes or films with necessary air and gas exchange have been used to prevent bulk evaporation as well as the edge effect. Examples of these products include Aeraseal™ Sealing Films and Breathe-Easy™ gas permeable sealing membranes for microtiter plates available from Diversified Biotech, Boston, Mass. However, such films are not automation friendly with the high throughput screening (HTS) procedures used in many laboratories. A commercially available device, Modular Incubator Chamber, was developed to eliminate the edge effect. Nine 96-well plates can be put in the chamber with customized tissue culturing conditions. One drawback to the device is that it has to be manually operated and does not meet high throughput screening requirements.

There is a need to provide a multiwell plate lid that can reduce or eliminate the edge effect. It would be desirable to provide a lid that is inexpensive to manufacture and is compatible with HTS screening requirements

SUMMARY OF INVENTION

One embodiment of present invention relates to methods and multiwell plates including a lid that reduces or minimizes the edge effect during assays. The multiwell plates include a frame that forms sidewalls of a plurality of wells arranged in a matrix and a lid having a plurality of openings therein.

Advantages of the invention will be apparent from the following detailed description. It is to be understood that both the foregoing general description and the following detailed description are exemplary and are intended to provide further explanation of the invention as claimed.

DETAILED DESCRIPTION

Before describing several exemplary embodiments of the invention, it is to be understood that the invention is not limited to the details of construction or process steps set forth in the following description. The invention is capable of other embodiments and of being practiced or being carried out in various ways.

The present invention relates to assay devices and methods, and in particularly to multiwell plates and lids for performing biological and chemical reactions. Certain embodiments of the present invention provide multiwell plates and lids that exhibit reduced edge effect. As used herein the term “edge effect” means a difference in evaporation from the wells bordering the outer periphery and corners of a multiwell plate compared to the evaporation from wells located in the interior portion of the plate. The multiwell plates and lids of the present invention are particularly useful for use in performing cell based assays.

Figure 1:
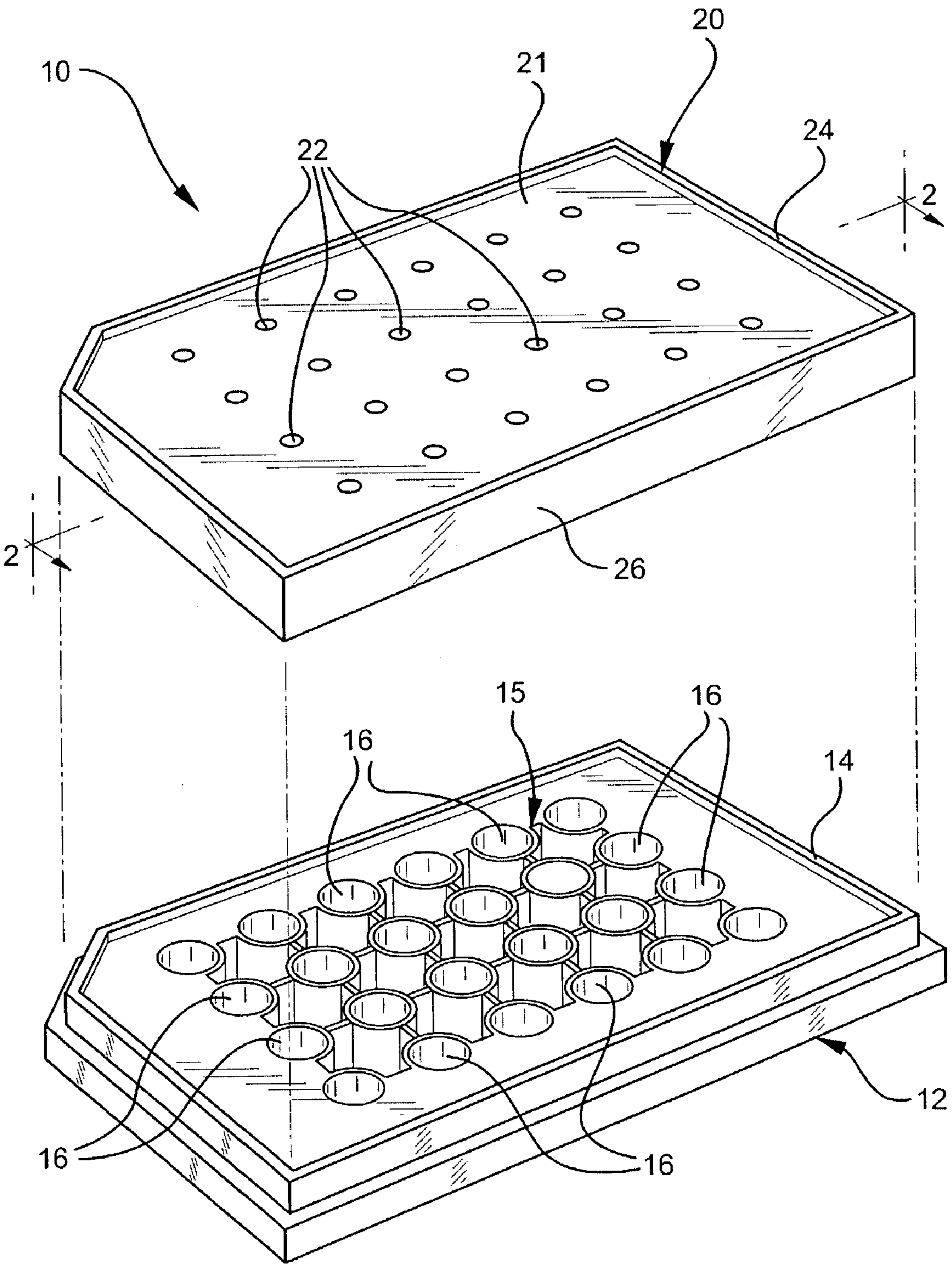
FIG. 1 is an exploded perspective view of a multiwell plate and lid according to one embodiment of the invention.

An exemplary embodiment of an assay device is shown in FIG. 1 and designated generally as 10. The assay device 10 includes a plate 12 having a frame 14 and a plurality of wells 15 arranged in a matrix. The wells 15 include outer wells 16 arranged along the outer periphery and corners of the plate. The plate 12 dimensionally conforms to the industry standard footprint for multiwell plates, namely the width and length dimensions of the plate are preferably standardized at approximately 85 mm and 128 mm, respectively. The assay device 10 further includes a planar, rigid lid 20 for covering the plurality of wells 15. The lid 20 includes a plurality of openings 22 through the lid surface 21 adapted to allow gas exchange and controlled, minimized evaporation that occurs only through the openings 22. As used herein, evaporation only through the openings means that no additional material such as a membrane or filter covers the openings. The material used to manufacture the lid 20 can be the same as that of the multiwell plate or can be any material which can easily be formed with holes or openings through the lid. An example of a material that can be used to make is polystyrene or any polymer that is suitable for the application.

In preferred embodiments, the openings 22 are uniformly distributed across the surface 21 of the lid 20 in an array.

While the present invention should not be limited to a particular number or size of openings, in preferred embodiments, the plate includes at least 10 openings, preferably 15 or more openings. In certain embodiments, it may be desirable to provide 20 or more openings, for example, 24 openings. In still other embodiments, it may be desirable to provide at least 40 openings, for example 42 openings. In other embodiments, the lid may include up to 90 openings. The size or diameter of the openings should be at least 0.005 inches, and preferably at least 0.010 inches. In certain preferred embodiments, the size or diameter of the openings is 0.014 inches. It will be understood that larger sized openings can be used, which would reduce the number of openings required. Thus, the size or diameter of the openings could be at least 0.015 inches, 0.020 inches, 0.025, or up to 0.050 inches. Preferably, the lids openings are circular in shape. However, the openings could also be oval, square, rectangular, triangular or other shapes. As used herein, the size or diameter of the openings refers to the largest distance between edges of the openings, and use of the term "diameter" does not mean that the opening must be circular.

In certain embodiments, the lid 20 includes a raised peripheral rib 24 adapted to allow another multiwell plate to be stacked on top of the lid without contacting the openings 22 on the surface of the lid during shipping and storage. According to certain embodiments, the height of the peripheral rib 24 should be at least about 0.025 inches and preferably at least about 0.037 inches. In preferred embodiments, the lid 20 further includes a skirt 26 having a height that is approximately the same height as a standardized microplate. This height is typically at least about 0.190 inches for a shallow lid and at least about 0.310 inches for a deep lid. It will be understood, of course, that the present invention should not be limited to a particular rib or skirt height. According to certain embodiments, the lid 20 preferably has a built in seal 28 on the periphery of the underside 30 of the lid, the seal 28 adapted to prevent evaporation through the edges of the lid. Preferably, the seal 28 is made from materials including a soft copolymer such as a thermoplastic elastomer. The material used for the preferably has a sufficient level of water resistance so that it does not stick to the multiwell plate body when the moisture content is high.

Figure 2:
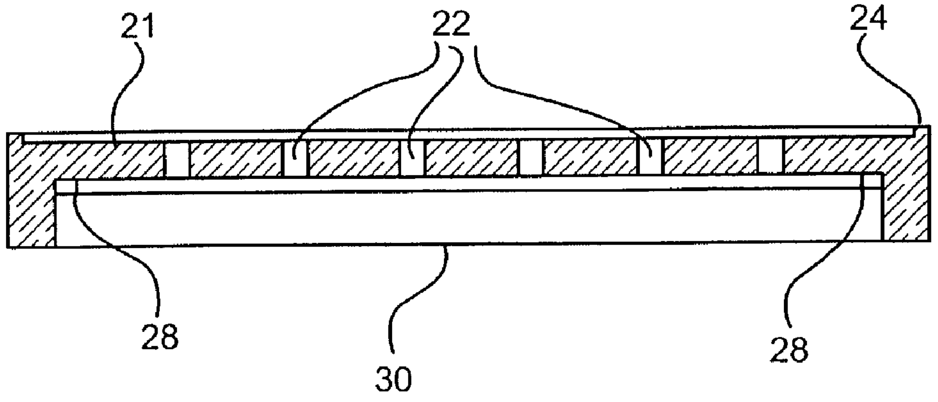
FIG. 2 is a cross sectional view of the lid taken along line 2-2 in FIG. 1.
Figure 3:
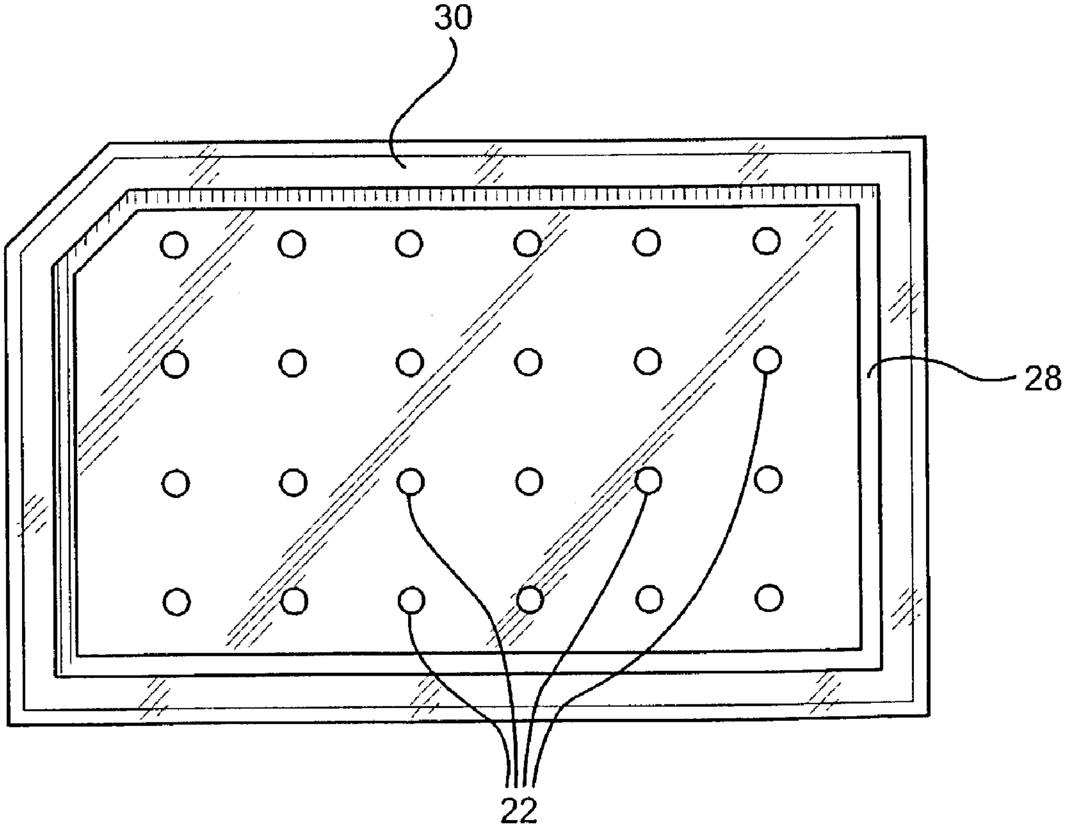
FIG. 3 is a top view of the underside of lid according to one embodiment of the invention.
Figure 4:
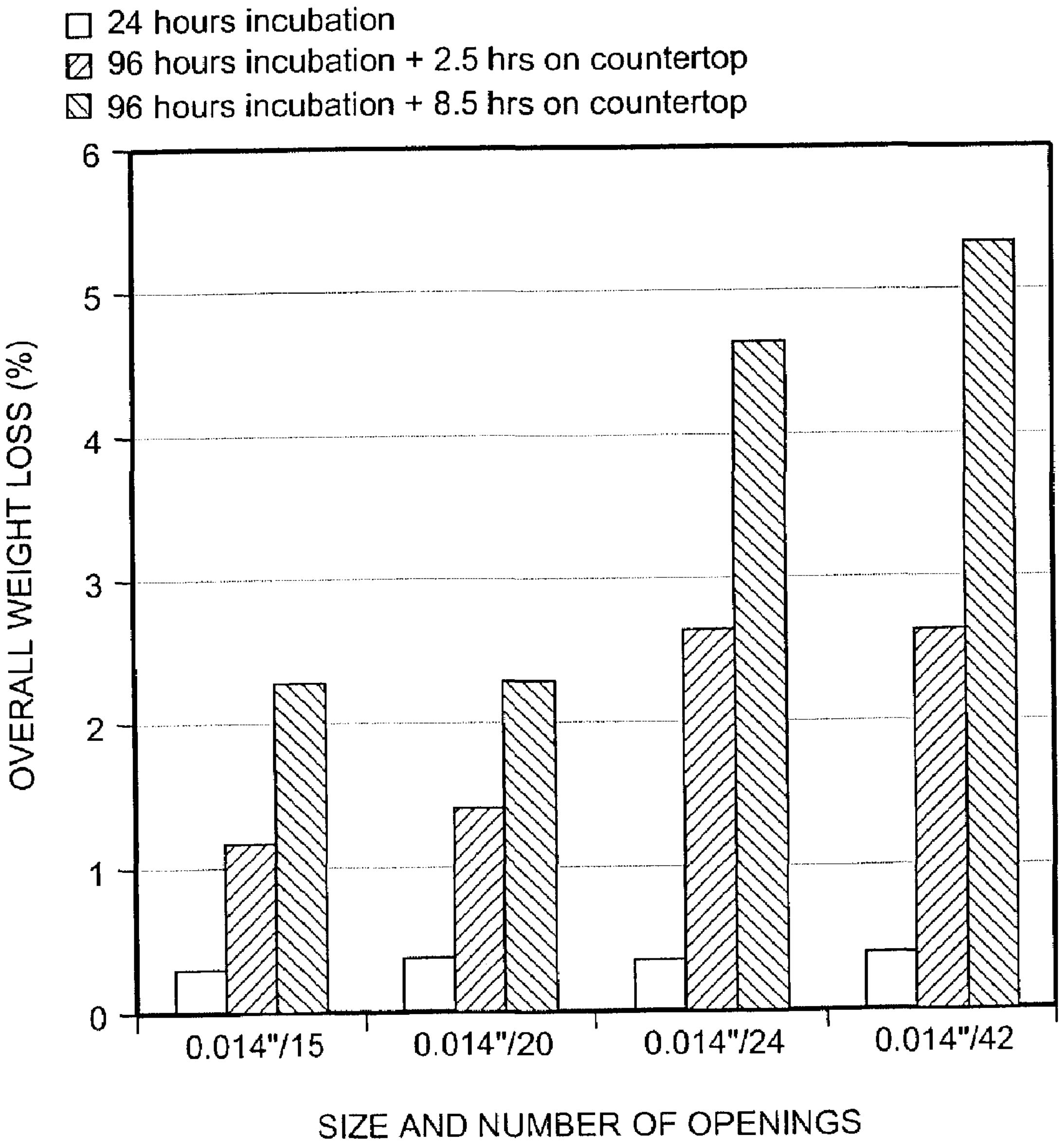
FIG. 4 is a graph showing evaporation data from lids made according to the present invention.

The lid 20 can be made using conventional plastic or glass forming processes. If the lid is made from a plastic or polymeric material, the lid can be injection molded. The lid can be formed and the openings can be formed in the lid at the same time. Alternatively, the openings can be formed using a separate step such as drilling. Preferably, the controlled size and number of openings will be molded through the injection molding process. As shown in FIGS. 2 and 3, the seal 28 around the peripheral edge of the underside the lid can be over molded with a soft copolymer material. The seal 28 prevents evaporation through the edges of the lids, and any evaporation or breathing will be only through the openings in the lid. The material used for the seal should allow minimum force to remove the lid under high humidity and temperature. The lid can be lifted by a robotic hand or by a suction cup. If a suction cup is used, there should not be openings in the area where the suction cup is in contact with the lid.

While any number of wells may be possible in the disclosed invention, preferably, the plate has greater than five wells. Standardized multiwell plates typically have 6, 12, 24, 96, 384, or 1536 wells. Further, the spacing between rows, both in the x and y direction of the plate, is preferably modeled off the industry standard multiwell plate. For example, the preferred spacing between rows for a 384 well plate is one half (approximately 4.5 mm) the center to center spacing between rows of a 96 well plate (approximately 9 mm). Similarly, the spacing for a 1536 well plate is preferably one fourth (approximately 2.25 mm) the center to center row spacing for a 96 well plate. This way, auxiliary equipment such as multiple pipetters or robots designed for use with 96 well plates may be easily adjusted for use with these higher well density plates. Additionally, row numbering for a 384 well plate (16×24 mutually perpendicular rows) and a 1536 well plate (32×48 mutually perpendicular rows) are multiples of a 96 well plate (8×12 mutually perpendicular rows). The sidewalls may be any height, depending on the desired volume per well.

Multiwell plates with lids according to the present invention can direct the evaporation to make the evaporation more uniform and reduce or eliminate the edge effect. Unlike conventional lids, the lid of the present invention has a plurality of unobstructed openings. In especially preferred embodiments, the size of the openings is 0.014 inches in diameter or larger. Depending on the nature experiments to be performed with the multiwell plate, the size and the number of openings can be manipulated. The built-in seal in the underside of the microplate prevents any evaporation from the edge other than through the openings in the lid. With a controlled size and number of openings, a minimized and controlled evaporation and breathing can be obtained uniformly over the entire plate.

The lids of the present invention are simple and inexpensive to produce. Unlike commercially available lids, the lid of the present invention does not require an expensive breathable membrane in the opening.

Without intending to limit the invention in any manner, the invention will be more fully understood and described by the following examples.

EXAMPLES

Overall Evaporation Test

Corning 1536-well clear bottom multiwell plates were used for the experiment. De-ionized water with yellow food coloring was used for the evaporation test. Four lids with different openings (15, 20, 24, 42, see Table 1) in diameter of 0.014" were tested. The total open area was calculated by multiplying the area of each opening and the number of openings. The conditions of the test were 37° C., 95% relative humidity (RH), and 5% $CO_2$ in an incubator. FIG. 3 shows the evaporation from each of the four plates with lids for varying times. The overall evaporation from each of four 1536 well multiwell plates covered by each of the four lids was less than 1%. After an additional 72 hours (96 hours total) incubation plus setting on the countertop for 3.5 hours, the overall evaporation was less than 3%. After an additional 19 hours (26.5 hours total on the countertop) on the countertop, the highest overall evaporation was approximately 5.5%. In typical experimental conditions, 5~7 hours will be the maximum length of time that multiwell plates with covers will be left on a countertop.

TABLE 1

Size and number of holes with the Top Vent lids

| Lids | Size of openings | Number of openings | Total open area (square inches) |
|---|---|---|---|
| 8 | 0.014" | 42 | 0.0065 |
| 9 | 0.014" | 24 | 0.0037 |
| 10 | 0.014" | 20 | 0.0031 |
| 11 | 0.014" | 15 | 0.0023 |

Edge Effect

Visual inspection of the wells of the multiwell plates showed that the 1536 multiwell plates covered with the lids of referred to in Table 1 did not show noticeable empty wells or significant reduced volumes in the wells adjacent the edges and corners of the multiwell plates (which were identified with the colored water in the wells). In contrast, multiwell plates covered with regular lids (a solid lid without a seal or openings) showed significant empty wells in the first and second rows of wells adjacent the four edges and corners. In addition multiwell plates covered with regular lids exhibited an overall evaporation of greater than 10% after approximately 48 hours of incubation and approximately 8 hours on the countertop.

Cell Culture Test

Lids were tested using a cell culture test to determine if the cells were healthy within 24 hours of incubation. Lids should allow the wells to breathe so that the cells should be healthy after 24 hours incubation. 1536-well multiwell plates were seeded with 1.5×103 Cho cells in 7 μl media per well and the lids referred to in Table 1 were placed on the multiwell plates. All of the multiwell plates were incubated at 37° C. for a period of 24 hours. At the end of the incubation period, the multiwell plates were checked for cell attachment before a WST1 cell proliferation assay was performed. Inspection of the cells showed that the cells had attached and appeared to be healthy. The wells appeared to be nearly confluent. None of the plates exhibited a clear indication of edge effect.

Air-Born Contamination Test

Five lawn multiwell plates (sterile) with four lids (sterile) with 42, 24, 20, and 15 openings and a regular lid were used for the test. LB Agar, Miller (Dehydrated) including tryptone, yeast extract, sodium chloride, and agar was used for the test. A solution of was prepared by adding 10 grams of tryptone, 5 grams of yeast extract, 10 grams of sodium chloride, and 15 grams of agar to 1000 ml of deionized water and boiling to dissolve the additives. 400 ml of the solution was sterilized at 121-124° C. for 20 minutes. The solution was transferred to five multiwell plates covered by the specific lids. Parafilm® was used to seal the multiwell plates from outside to ensure that no contamination entered the wells through the openings. Then the plates along with lid were kept on the countertop of the warm room (37° C.) for 72 hours. No bacterial contamination was found from any of the plates as the gel in each of the wells from the plates tested was clear as the fresh gel.

Volume Change Evaluation with Individual Wells

Three Corning 1536 clear microplates covered by a 42-hole lid, a 24-hole lid, and a regular lid were tested. The microplat for 24 hours before the measurements. Note that the evaporation of 24 hours on a counter top could be ten times higher than in an incubator. The result showed that the regular lid had the significant edge evaporation (up to 75%) from outside wells (top first row, bottom first row, and two first rows of side wells) while the 42-hole and 24-hole lids had more even evaporation with very low rate of approximately 20%.

These results show that the lids of the present invention showed significant less edge effect than the regular lids. No bacterial contamination was observed from lids of the present invention or from the regular lids after three days in a warm room (37° C.). No edge effect or contamination was observed from the cell based assay tests as evidenced by the existence of healthy cells after 24 hours incubation in a plate sealed with a lid according to the present invention. All the 42, 24, 20, and 15 openings are suitable for the lid. Depending on the requirements of particular applications, other numbers of openings could be provided as well.

It will be apparent to those skilled in the art that various modifications and variations can be made to the present invention without departing from the spirit or scope of the invention. Thus, it is intended that the present invention cover modifications and variations of this invention provided they come within the scope of the appended claims and their equivalents.

What is claimed is:

1. An assay device comprising:

a plate including a frame and a plurality of wells arranged in a matrix;

a removable planar, rigid lid having a surface and constructed so as to cover the plurality of wells, the lid including a plurality of openings uniformly distributed across the surface of the lid and sized, positioned and arranged so as allow gas exchange and controlled, minimized evaporation that occurs uniformly from the wells and only through the openings; and a built in seal on the peripheral edge of the underside of the lid, the lid constructed so that the built in seal contacts a surface of the plate and prevents evaporation through the edges of the seal, wherein the lid contains no membrane.

2. The assay device of claim 1, further including a raised peripheral rib adapted to allow a microplate to be stacked on top of the lid.

3. The assay device of claim 1, wherein the device is adapted for performing cell based assays.

4. The assay device of claim 1, wherein the seal is made from materials including a soft copolymer.

5. The assay device of claim 1, wherein lid includes at least 12 openings.

6. The assay device of claim 1, wherein the lid includes at least 42 openings.

7. The assay device of claim 5, wherein the openings have a diameter of at least 0.010 inches.

8. The assay device of claim 5, wherein the openings have a diameter of at least 0.014 inches.

9. A multiwell plate lid comprising:

a removable planar, rigid lid constructed so as to cover a plurality of wells of a multiwell plate the lid including a plurality of openings sized, positioned and arranged to allow gas exchange and controlled, minimized evaporation that occurs uniformly from the wells and only through the openings; and a built in seal on the peripheral edge of the underside of the lid, the lid constructed so that the built in seal contacts a surface of the plate and prevents evaporation through the edges of the seal, wherein the lid contains no membrane.

10. The multiwell plate lid of claim 9, further comprising: a raised peripheral rib adapted to allow a microplate to be stacked on top of the lid; and a skirt extending from the peripheral edge.

11. The multiwell plate lid of claim 10, wherein the seal is made from materials including a soft copolymer.

12. The multiwell plate lid of claim 11, wherein lid includes at least 24 openings.

13. The multiwell plate lid of claim 11, wherein the lid includes at least 42 openings.

14. The multiwell plate lid of claim 12, wherein the lid openings are at least 0.010 inches in diameter.

15. The multiwell plate lid of claim 13, wherein the openings are at least 0.014 inches in diameter.

16. The multiwell plate lid of claim 9, wherein the openings are evenly distributed across the lid.

* * * * *